United States Patent [19]

Miyazaki et al.

[11] Patent Number: 5,093,155

[45] Date of Patent: Mar. 3, 1992

[54] PROCESS FOR SIZING REINFORCING FIBER BY APPLYING SULFONE COMPOUNDS CONTAINING SULFONYL GROUPS AND SIZED REINFORCING FIBERS OBTAINED THEREBY

[75] Inventors: Makoto Miyazaki, Sakato; Yoshio Wakoh; Hiroshi Inoue, both of Iruma, all of Japan

[73] Assignee: Tonen Corporation, Japan

[21] Appl. No.: 442,292

[22] Filed: Nov. 28, 1989

[30] Foreign Application Priority Data

Nov. 29, 1988 [JP] Japan ................... 63-299606

[51] Int. Cl.$^5$ ............................................. B05D 3/12
[52] U.S. Cl. ................... 427/177; 427/388.5; 427/388.4; 427/385.5; 427/178; 427/389.8; 428/375; 428/366; 428/367; 428/392; 428/379
[58] Field of Search ............ 427/388.4, 388.5, 385.5, 427/177, 178, 389.8; 428/366, 367, 392, 379, 375

[56] References Cited

U.S. PATENT DOCUMENTS

| | | | |
|---|---|---|---|
| 3,632,391 | 1/1972 | Whitfield et al. | 428/270 |
| 3,634,130 | 6/1972 | Long et al. | 524/789 |
| 3,785,916 | 1/1974 | Turton et al. | 156/166 |
| 4,039,511 | 8/1977 | Wulff et al. | 260/49 |
| 4,549,920 | 10/1985 | Cogswell et al. | 156/181 |
| 4,608,304 | 8/1986 | Rosthauser | 428/378 |
| 4,764,397 | 8/1988 | Fischer et al. | 427/385.5 |
| 4,764,427 | 8/1988 | Hara et al. | 428/375 |
| 4,783,349 | 11/1988 | Cogswell et al. | 427/407.3 |
| 5,045,367 | 9/1991 | Bobsein et al. | 428/375 |
| 5,049,446 | 9/1991 | Blackwell | 428/375 |

FOREIGN PATENT DOCUMENTS 2289545  10/1975  France .
2073184A  3/1980  United Kingdom .

*Primary Examiner*—Michael Lusignan
*Assistant Examiner*—Diana L. Dudash
*Attorney, Agent, or Firm*—LoRusso & Loud

[57] ABSTRACT

A novel sulfone compound represented by the general formula (I) or (II) is disclosed. A sizing liquid containing the sulfone compound is applied to reinforcing fibers for improving compatibility thereof to a matrix resin into which the fibers are to be incorporated to form a fiber-reinforced composite material.

6 Claims, No Drawings

PROCESS FOR SIZING REINFORCING FIBER BY APPLYING SULFONE COMPOUNDS CONTAINING SULFONYL GROUPS AND SIZED REINFORCING FIBERS OBTAINED THEREBY

BACKGROUND OF THE INVENTION

This invention relates to a novel sulfone compound useful for surface-treating reinforcing fibers in producing a fiber-reinforced, thermoplastic resin composite material. The present invention is also directed to a process for surfacetreating reinforcing fibers using the above compound and to reinforced fibers obtained by the process.

Composite materials composed of reinforcing fibers and various matrixes such as synthetic resins, metals or ceramics have find wide applications such as aircraft parts, space apparatuses, precision machines, sport goods such as tennis rackets and golf shafts due to their excellent mechanical properties including specific strength and specific modulus of elasticity.

Various investigations have so far been conducted to improve the strength and modulus of fiber-reinforced composite materials. In general, in order to obtain the excellent properties of the reinforcing fibers, it has been believed to be of importance to enhance affinity and adhesion properties between the reinforcing fibers and matrix and, from this point of view, many sizing agents for activating the surface of reinforcing fibers have been proposed.

As such sizing agents, epoxy resin type sizing agents have so far been often employed. However, such sizing agents, which show excellent affinity and impregnation properties for thermosetting resin type matrixes and offer extremely favorable advantages, have the defect that they show poor wetting properties and impregnation properties when thermoplastic resins such as polyamides, polycarbonates, polyphenylene oxides, polyphenylene sulfides, polyether sulfones, polysulfones, polyether ether ketones and polyetherimides are used as the matrix resin. It follows that the adhesion between the reinforcing fibers and the matrix resin becomes poor, thus failing to offer desired physical properties.

Sulfur-containing, heat-resistant resins such as polyphenylene sulfide have recently been noted as matrix resins for fiber-reinforced composite materials because of their excellent heat resistance, flame resistance, chemical resistance and, in addition, less expensiveness and better moldability in comparison with other resins such as polyimide resins. However, the epoxy resin type sizing agents possess poor wetting properties and impregnation properties for the polyphenylene sulfide. In addition, since the molding temperature of polyphenylene sulfide is as high as 300° C. or above, thermal decomposition of the sizing agents can take place upon molding to cause generation of voids.

In order to solve these problems, the use of a polysulfone or a polyphenylene sulfide as a sizing agent for carbon fibers for use in carbon fiber-reinforced composite materials containing a polyphenylene sulfide as a matrix is proposed (for example, Japanese Unexamined Patent Publication Nos. 56-120730 and 56-90837). These sizing agents are superior to the epoxy resin type sizing agents in heat resistance, impregnation properties for polyphenylene sulfide, and the like.

However, these sizing agents still involve the following problems. That is, in the case of using such a polymer as polysulfone or a polyphenylene sulfide as a sizing agent, carbon fiber bundles lose their intrinsic flexibility and become rigid due to the large modulus of the sizing agent. As a result, it becomes impossible to sufficiently deposit the sizing agent. In addition, since there are available no suitable solvents capable of readily dissolve the polyphenylene sulfide at ordinary temperature, a special coating method must be employed in order to uniformly coat the sizing agent on carbon fiber bundles and to control the amount of the deposited sizing agent.

SUMMARY OF THE INVENTION

In accordance with one aspect of the present invention there is provided a sulfone compound represented by the following general formula (I) or (II):

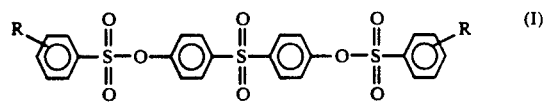

wherein R represents hydrogen or lower alkyl;

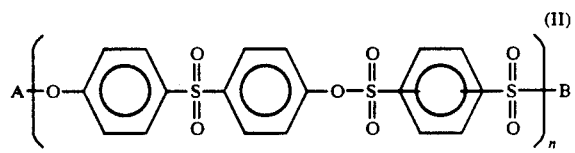

wherein A represents hydrogen or

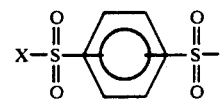

where X represents halogen or hydroxyl, B represents halogen, hydroxyl or

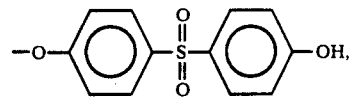

and n represents an integer of 1 or more.

In another aspect, the present invention provides a process for treating reinforcing fibers, which comprises applying to the reinforcing fibers a sizing liquid containing a sulfone compound represented by the following general formula (I) or (II):

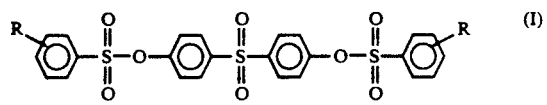

wherein R represents hydrogen or lower alkyl;

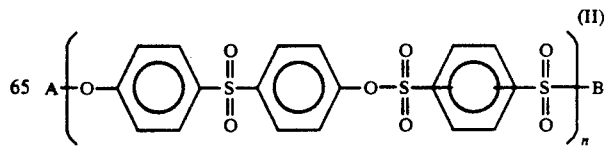

wherein A represents hydrogen or

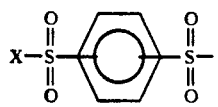

where X represents halogen or hydroxyl, B represents halogen, hydroxyl or

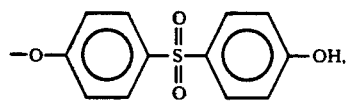

and n represents an integer of 1 or more.

The present invent invention also provides surface-treated, reinforcing fibers obtained by the above process.

The present invention will now be described in detail below.

DESCRIPTION OF THE PREFERRED EMBODIMENTS

In the above general formulae (I) and (II), the alkyl group represented by R is preferably a C1-C3 alkyl group, the halogen atom represented by X is preferably a chlorine atom or a bromine atom, and n is preferably an integer of 1 to 10.

The sulfone compound represented by the general formula (I), or 4,4'- dibenzenesulfonyloxydiphenylsulfone or its alkyl derivative, can be synthesized, for example, according to the following reaction formula:

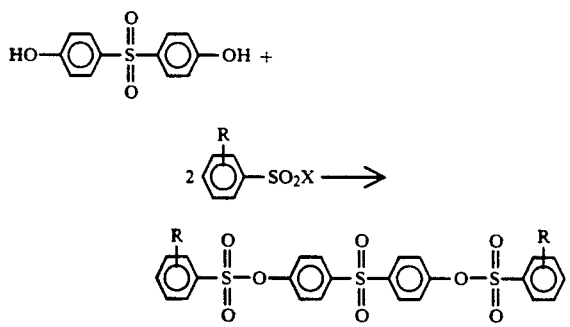

wherein X represents a halogen atom such as Cl or Br, and R is the same as defined hereinbefore.

That is, the sulfone compound can be easily obtained by reacting bisphenol S with benzenesulfonyl halide in an organic solvent, and extracting the thus-obtained product from the reaction mixture using an organic extraction solvent. In this case, N-methylpyrrolidone, α-pyrrolidone, etc. are preferably used as the reaction solvent, and toluene, xylene, etc. are preferably used as the extracting solvent. Molar ratio of bisphenol S to benzenesulfonyl halide is preferably 1 : 2 to 1 : 5.

The above reaction may be carried out at 50° to 200° C. for 0.5 to 10 hours, preferably from 1 to 5 hours. After completion of the reaction, the reaction mixture is cooled to form a precipitate, and the precipitate is extracted with the aforesaid organic extraction solvent to obtain a reaction product containing as a major component the compound of the formula (I).

The sulfone compound represented by the general formula (II) can be obtained by reacting, for example, bisphenol S with benzenedisulfonyl halide. In this case, too, the reaction is carried out at an elevated temperature in an organic solvent as is the same with the aforesaid reaction between bisphenol S and benzenesulfonyl halide, and extraction of the reaction mixture with an organic solvent yields a reaction product containing as a major component the sulfone compound of the formula (II). The molar ratio of bisphenol S to benzenedisulfonyl halide is in the range of from 5 : 1 to 1 : 5, which is properly selected depending upon the kind of the end product.

The sulfone compound according to the present invention may be suitably used as a sizing agent for reinforcing fibers in the form of a solution in an organic solvent such as acetone, methyl ethyl ketone or a halogenated hydrocarbon or in the form of an aqueous emulsion using a surfactant. One or more aids commonly added to known sizing agents may be used, if desired.

The sizing treatment for the deposition of the sizing agent onto reinforcing fibers may be effected by a dipping process, a spraying process, a process using a roller or any other suitable process.

Reinforcing fibers to be treated according to the present invention include, for example, carbon fibers, glass fibers, boron fibers, ceramic fibers and metal fibers. Both continuous and chopped fibers may be used. As the carbon fibers, there may be used any of so-called carbonized type and graphitized type obtained by treating precursor fibers, such as of pitch series, acrylic series or cellulose series, for rendering them infusible or flame-resistant in a known manner, then calcining the treated fibers at 800–3000° C. in an inert gas atmosphere. Carbon fibers whose surface is oxidation-treated are desirably used. The ceramic fibers include, for example, silicon carbide fibers, silicon nitride fibers, boron nitride fibers and alumina fibers.

The amount of the sizing agent to be deposited onto the reinforcing fibers is generally 0.1 to 10 wt %, preferably 0.5 to 5 wt %, as solids. If the deposition amount is less than the 0.1 %, desired wetting properties and impregnation properties cannot be obtained. Too large an amount in excess of 10 wt % is undesirable because fiber bundles become rigid and difficult to handle and because the physical properties of the resulting composite materials are deteriorated.

The reinforcing fibers thus treated with the sizing agent may be wound around a bobbin, or directly fed continuously to a composite-molding step.

The sizing agent of the present invention is excellent in wetting properties and impregnation properties for the surface of reinforcing fibers and, in addition, excellent in wetting properties and impregnation properties for various matrix resins, and shows a markedly improved impregnation properties particularly for sulfur-containing, heat-resistant resins such as polyphenylene sulfide, polyether sulfone, and polysulfone.

The reinforcing fibers thus treated with the sizing agent are very suited for the production of a composite material in which the fibers are composited within a matrix resin. Any commonly employed process, such as a filament-winding process, a prepreg process, a sheet-molding proccess or an injection molding process may be adopted for the production of such a composite material. For example, the injection molding process comprises the steps of cutting reinforcing fiber bundles treated with the sizing agent into a length of 1 to 20 mm, blending the cut fiber bundles with polyphenylene sulfide in a blender, pelletizing the blend using an extruder, and then molding the pellets by means of an injection molding machine.

The sizing agent according to the present invention shows excellent wetting properties and impregnation properties for both reinforcing fibers and matrix resins, particularly matrix resins of sulfur-containing, heat-resistant resins such as polyphenylene sulfide resins, does not spoil flexibility of the reinforcing fibers, and has a good solvent solubility. Hence, heat-resistant composite materials compounded with the reinforcing fibers treated with the sizing agent according to the present invention are free of voids and have markedly improved mechanical properties.

The following examples will further illustrate the present invention.

EXAMPLE 1

50 g of bisphenol S was dissolved in 200 g of N-methylpyrrolidone, to which 40 g of triethylamine was added. After addition of 70 g of benzenesulfonyl chloride, the mixture was reacted at 130° C. for 2 hours. The reaction mixture was poured into 1 liter of distilled water to precipitate a solid product. After air-drying, this solid product was extracted with 500 ml of toluene, and toluene was distilled off from the extract using a rotary evaporator to obtain a solid product. Identification of this product by GPC (gel permeation chromatography), IR and NMR revealed that 4,4'-dibenzenesulfonyloxydiphenylsulfone was a major component of the product. The DSC (differential scanning calorimetry) measurement revealed that the melting point of the product was 112° C.

Carbon fibers, Toreca T-300 6K (product of Toray Industries, Inc.), were calcined at 800° C. for 5 hours, subjected to continuous electrolytic oxidation, then dipped in a 1 wt % solution of the above sulfone compound in acetone, followed by drying at 100° C. in an oven to obtain surface-treated carbon fibers. The fibers were subjected to Soxhlet's extraction using methyl ethyl ketone (MEK) for measuring the amount of deposited sizing agent. The amount was found to be 1.5 % based on the weight of the non-treated fibers. The surface-treated carbon fibers showed an excellent flexibility and good handling properties. The handling properties were evaluated from the results of rubbing test conducted as follows:

(A) Rub with fibers

Using a rubbing tester made by Toyo seiki K.K., sample fibers are rubbed with each other under the conditions of 500-time reciprocations, 100 g/300 filaments in load, 45 in internal angle, one time in twist, 20 mm in rubbing length, and 200 reciprocations/minute in rubbing speed.

(B) Rub with metal

Using TM-model cohesion tester made by Daiei Kagaku Seiki K.K., sample fibers are rubbed with a chromium-plated metallic comb under the conditions of 300-time reciprocations at a rate of 150 reciprocations/minute, 200 g/3000 filaments in load, $\theta = 150°$, and 30 mm in rubbing length. The results were scored in terms of 5-point grades according to the following rate.
5...no fluffs and no fiber breakage
4...slight fluffs
3...some fluffs
2...many fluffs and some fiber breakage
1...breakage A layer of the surface-treated carbon fibers oriented in parallel with each other was sandwitched by polyphenylene sulfide sheets (T-1, product of Toplain Inc.), followed by preliminary heating at 300° C for 5 minutes and pressing for 5 minutes to obtain a composite material of about 1 mm in thickness and 50 volume % in carbon fiber content. The thus obtained composite material was subjected to void content measurement and tensile test according to ASTM D 638. The results are shown in Table 1.

EXAMPLE 2

A sizing agent was synthesized under the same conditions as in Example 1 except for using 48 g of metabenzenedisulfonyl chloride in place of benzenesulfonyl chloride, and carbon fibers were dipped in a 0.5 wt % solution of the sizing agent in acetone. Preparation of a composite material and evaluation of physical properties of the composite material were also conducted in the same manner as in Example 1. The results are shown in Table 1.

EXAMPLE 3

Dipping treatment of carbon fibers, preparation of a composite material and evaluation of physical properties of the composite material were conducted in the same manner as in Example 2 except for changing the amount of metabenzenedisulfonyl chloride to 96 g. The results are shown in Table 1.

EXAMPLE 4

Dipping treatment of carbon fibers, preparation of a composite material and evaluation of physical properties of the composite material were conducted in the same manner as in Example 2 except for changing the amount of metabenzenedisulfonyl chloride to 24 g. The results are shown in Table 1.

EXAMPLE 5

Synthesis of a sizing agent, dipping treatment of carbon fibers, preparation of a composite material and evaluation of physical properties of the composite material were conducted in the same manner as in Example 2 except for using orthobenzene disulfonyl chloride in place of metabenzenedisulfonyl chloride. The results are shown in Table 1.

EXAMPLE 6

Preparation of surface-treated carbon fibers, preparation of a composite material, and evaluation of physical properties or the composite material were conducted in the same manner as in Example 1 except for dipping carbon fibers in a 3% solution of the sizing agent in acetone. The results thus obtained are shown in Table 1.

EXAMPLE 7

Petroluem pitch was subjected to thermal polycondensation reaction to obtain a carbonaceous pitch having a softening point of about 235° C. and an optical anisotropy of about 55%. This pitch was subjected to a cylindrical centrifugal separator to separate a pitch having a softening point of 265° C. and an optical anisotropy of 98 %.

The thus obtained pitch was spun, rendered infusible and calcined to obtain carbon fibers. Filament strength and modulus of elasticity of the carbon fibers were found to be 353 kg/mm² and 50,400 kg/mm², respectively. Subsequently, a bundle of 3000 filaments of the carbon fibers was subjected to electrolytic oxidation. Then, preparation of surface-treated carbon fibers, preparation of a composite material, and evaluation of physical properties of the composite material were conducted in the same manner as in Example 1. The results are shown in Table 1.

COMPARATIVE EXAMPLE 1

Preparation of a composite material and evaluation of physical properties of the composite material were conducted in the same manner as in Example 1 except for omitting the dipping treatment. The results are shown in Table 1.

COMPARATIVE EXAMPLE 2

Preparation of surface-treated carbon fibers, preparation of a composite material, and evaluation of physical properties of the composite material were conducted in the same manner as in Example 1 except for dipping carbon fibers in a 7 wt % solution of a sizing agent of VICTREX PEX (a trademark of ICI for a polythersulfone) in methylene chloride. The results are shown in Table 1.

COMPARATIVE EXAMPLE 3

Preparation of surface-treated carbon fibers, preparation of a composite material, and evaluation of physical properties of the composite material were conducted in the same manner as in Example 1 except for dipping carbon fibers in 2 wt % solution of a sizing agent of EPIKOTE 828 (a trademark of Yuka Shell K.K. for a diglycidylether of bisphenola) in acetone. The results are shown in Table 1.

EXAMPLES 8-10

The surface-treated carbon fibers obtained in Example 6 were cut into 3-mm short fibers using a roving cutter made by Yamamoto Giken Kogyosha to obtain chopped fibers. Then, polyphenylene sulfide T-4 made by Toplain Inc. was introduced into a biaxial extruder TEX2 (45 mm OD ) made by Japan Steel Works, Ltd. from a one-stage feeder, and the above-described chopped fibers from a two-stage feeder, to obtain carbon fibers/PPS compound pellets. Upon production of the compound, striking-through of the chopped fibers from the feeder was good,and the resulting pellets did not undergo foaming phenomenon such as air bubble formation, thus a good compound was obtained. Three kinds of samples having carbon fiber contents of 20 wt %, 30 wt % and 40 wt %, respectively, were prepared.

The thus obtained compound was injection-molded using an injection molding machine, J75SA, made by Japan Steel Works Ltd. to prepare test pieces for tests on physical properties. Bending test was conducted as to the resulting test pieces according to ASTM D-790. The results are shown in Table 2.

EXAMPLE 11

Preparation of compound, preparation of test piece and bending test were conducted in the same manner as in Example 9 using the surface-treated carbon fibers obtained in Example 7. The results are shown in Table 2.

EXAMPLES 12-14

Preparation of a glass fibers/PPS compound, preparation of test piece and bending test were conducted in the same manner as in Examples 8-10 except for using ER 2310 made by Asahi Fiberglass Co. as glass fibers.

COMPARATIVE EXAMPLE 4

Preparation of a compound, preparation of a test piece and a bending test were conducted in the same manner as in Example 9 using the surface-treated carbon fibers obtained in Comparative Example 3. The results are shown in Table 2.

COMPARATIVE EXAMPLE 5

Preparation of a compound, preparation of a test piece and a bending test were conducted in the same manner as in Example 13 except for omitting the dipping treatment with the sizing agent. The results are shown in Table 2.

The major sulfone products obtained in Examples 1-6 are as follows:

Examples 1 and 6: The compound of the formula (I) in which R is hydrogen (molecular weight: 531);

Example 2: The compound of the formula (II) in which A is hydrogen, B is hydroxyl and n is 2 (molecular weight: 923);

Example 3: The compound of the formula (II) in which A is

B is hydroxyl and n is 1 (molecular weight: 691);

Example 4: The compound of the formula (II) in which A is hydrogen, B is

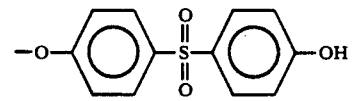

and n is 2 (molecular weight 1155);

Example 5: The compound of the formula (II) in which A is hydrogen, B is hydroxyl and n is 2 (molecular weight: 923).

TABLE 1

| | Amount of Deposited Sizing Agent (wt %) | Handling Properties Fiber/Fiber | Handling Properties Fiber/Metal | Voids (%) | Tensile Strength (kg/mm²) | Tensile Modulus of Elasticity (kg/mm²) |
|---|---|---|---|---|---|---|
| Ex. 1 | 1.5 | 5 | 4 | 0 | 178 | 12,400 |
| Ex. 2 | 1.2 | 4 | 4 | 0.8 | 172 | 12,300 |
| Ex. 3 | 0.9 | 4 | 4 | 0.1 | 161 | 12,500 |
| Ex. 4 | 0.8 | 4 | 5 | 0 | 178 | 12,100 |
| Ex. 5 | 1.0 | 4 | 4 | 1.2 | 166 | 12,100 |

TABLE 1-continued

| | Amount of Deposited Sizing Agent (wt %) | Handling Properties | | Voids (%) | Tensile Strength (kg/mm²) | Tensile Modulus of Elasticity (kg/mm²) |
|---|---|---|---|---|---|---|
| | | Fiber/Fiber | Fiber/Metal | | | |
| Ex. 6 | 3.8 | 5 | 5 | 0.6 | 173 | 11,900 |
| Ex. 7 | 1.4 | 4 | 4 | 0 | 151 | 24,800 |
| Comparative Ex. 1 | 0 | 2 | 1 | 2.6 | 148 | 12,100 |
| Comparative Ex. 2 | 2.7 | 2 | 3 | 1.7 | 160 | 12,300 |
| Comparative Ex. 3 | 2.1 | 5 | 4 | 4.3 | 127 | 11,800 |

TABLE 2

| | Kind of Reinforcing Fibers | Content of Reinforcing Fibers (wt %) | Bending Strength (Kg/mm²) | Bending Modulus of Elasticity (Kg/mm²) |
|---|---|---|---|---|
| Example 8 | carbon fibers | 20 | 27.2 | 2160 |
| Example 9 | " | 30 | 31.5 | 2970 |
| Example 10 | " | 40 | 33.9 | 3400 |
| Example 11 | " | 30 | 29.3 | 3780 |
| Example 12 | glass fibers | 20 | 20.8 | 1020 |
| Example 13 | " | 30 | 24.2 | 1340 |
| Example 14 | " | 40 | 26.6 | 1670 |
| Comparative Example 4 | carbon fibers | 30 | 24.0 | 2430 |
| Comparative Example 5 | glass fibers | 30 | 19.8 | 1010 |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A process for sizing reinforcing fibers, which comprises applying a sizing liquid to the surfaces of the reinforcing fibers, said sizing liquid containing a sulfone compound represented by the following general formula (I) or (II):

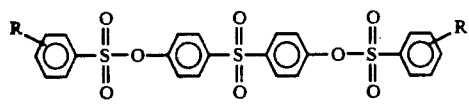 (I)

wherein R represents hydrogen or lower alkyl;

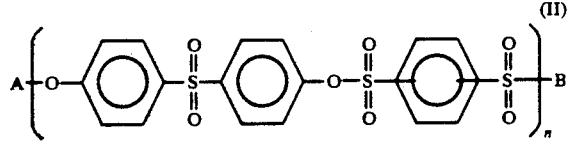 (II)

wherein A represents a hydrogen atom or

where X represents halogen or hydroxyl, B represents halogen, hydroxyl or

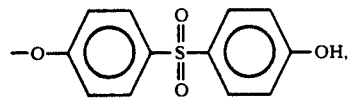

and n represents an integer of 1 or more.

2. Sized reinforcing fibers obtained by a process according to claim 1.

3. The process of claim 1 wherein the amount of said sizing liquid applied to the reinforcing fibers is 0.1 to 10 weight % solids based on the weight of the non-treated fibers.

4. The process of claim 1 wherein the amount of said sizing liquid applied to the reinforcing fibers is 0.5 to 5 weight % solids based on the weight of the non-treated fibers.

5. The process of claim 3 wherein said reinforcing fibers are suitable for reinforcing synthetic resins, metal or ceramics.

6. The process of claim 1 further comprising winding the sized fibers on a bobbin.

* * * * *